US007257186B2

(12) United States Patent
Bruder et al.

(10) Patent No.: US 7,257,186 B2
(45) Date of Patent: Aug. 14, 2007

(54) IMAGING METHOD FOR A MULTI-SLICE SPIRAL CT SCAN, AND A COMPUTER TOMOGRAPHY UNIT FOR CARRYING OUT THIS METHOD

(75) Inventors: Herbert Bruder, Hoechstadt (DE); Guenter Lauritsch, Erlangen (DE); Karl Stierstorfer, Erlangen (DE); Kwok Tam, Edison, NJ (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/686,629

(22) Filed: Oct. 17, 2003
(Under 37 CFR 1.47)

(65) Prior Publication Data
US 2004/0264630 A1    Dec. 30, 2004

(30) Foreign Application Priority Data
Oct. 18, 2002    (DE) ................ 102 48 766

(51) Int. Cl.
*A61B 6/03* (2006.01)
(52) U.S. Cl. ................ 378/15; 378/4; 378/901
(58) Field of Classification Search .......... 378/4, 378/8, 15, 901
See application file for complete search history.

(56) References Cited

U.S. PATENT DOCUMENTS

| | | | | |
|---|---|---|---|---|
| 6,018,561 | A * | 1/2000 | Tam .............. | 378/4 |
| 6,078,638 | A * | 6/2000 | Sauer et al. .......... | 378/4 |
| 6,084,937 | A | 7/2000 | Tam et al. | |
| 6,324,245 | B1 * | 11/2001 | Tam .............. | 378/4 |
| 6,574,297 | B2 * | 6/2003 | Tam .............. | 378/15 |
| 2003/0081715 | A1 * | 5/2003 | Tam .............. | 378/4 |

OTHER PUBLICATIONS

Hiroyuki Kudo et al. "Cone-beam filtered-backprojection algorithm for truncated helical data." IOP Publishing Ltd. *Phys. Med. Biol.* 43 (1998) 2885-2909.
Marc Kachelrieβ et al., "Advanced single-slice rebinning in cone-beam spiral CT", Jan. 12, 2000, pp. 754-772.
S. Schaller et al., "Novel approximate approach for high-quality image reconstruction in helical cone beam CT at arbitrary pitch", 2001, pp. 113-127.
Karl Stierstorfer et al., "Segmented multiple plane reconstruction: a novel approximate reconstruction scheme for multi-slice spiral CT", Jul. 17, 2002, pp. 2571-2581.
K. Sourbelle et al., "Performance Evaluation of Exact Cone-Beam Algorithms for the Long-Object Problem in Spiral Computed Tomography", Oct. 30-Nov. 2, 2001, pp. 153-156.
Hiroyuki Kudo et al., "Quasi-Exact Filtered Backprojection Algorithm for Long-Object Problem in Helical Cone-Beam Tomography", Oct. 2000, pp. 902-921.
K. C. Tam, "Exact local regions-of-interest reconstruction in spiral cone-beam filtered-backprojection CT: theory", 2000, pp. 506-519.
Günter Lauritsch et al., "Exact local regions-of-interest reconstruction in spiral cone-beam filtered-backprojection CT: numerical implementation and first image results", 2000, pp. 520-532.

\* cited by examiner

*Primary Examiner*—Edward J. Glick
*Assistant Examiner*—Chih-Cheng Glen Kao
(74) *Attorney, Agent, or Firm*—Harness, Dickey & Pierce, P.L.C.

(57) ABSTRACT

An imaging method is disclosed for a multi-slice spiral CT scan. A CT unit is disclosed for carrying out this method. In the method, the filtering may be formed by use of multiple applications of a ramp filter and a masking operation to a projection image in a different sequence. The CT unit may include, for filtering purposes, multiple applications of a ramp filter and a masking operation to a projection image in a different sequence.

16 Claims, 4 Drawing Sheets

IMAGING METHOD FOR A MULTI-SLICE SPIRAL CT SCAN, AND A COMPUTER TOMOGRAPHY UNIT FOR CARRYING OUT THIS METHOD

The present application hereby claims priority under 35 U.S.C. §119 on German patent application number DE 102 48 766.9 filed Oct. 18, 2002, the entire contents of which are hereby incorporated herein by reference.

FIELD OF THE INVENTION

The invention generally relates to an imaging method for a multi-slice spiral CT scan. Preferably, am object to be examined is scanned with reference to its absorption behavior by a rotating ray bundle moving in the direction of the axis of rotation, and the measured absorption data is collected. In order to reconstruct a volumetric image from the measured data, the latter are filtered and the filtered data are subsequently back-projected in three dimensions in order to generate a volumetric image of the object to be examined. The volumetric image represent absorption values, obtained from the data, of the voxels belonging to the volume of the object to be examined, for the radiation of the ray bundle. The invention also generally relates to a CT unit for carrying out this method and having appropriate imaging device.

BACKGROUND OF THE INVENTION

It is known to make use in computer tomography of multi-slice detectors and ray bundles with cone beam geometry for the purpose of scanning objects to be examined, in particular patients. In order to reconstruct a volumetric image including a multiplicity of small volume elements (=voxels), it is necessary to take account of the cone beam geometry in the now three-dimensional image reconstruction.

Such reconstruction algorithms for multi-slice spiral CT can be divided into the two classes of the approximative algorithms and the exact methods. Reference may be made to the following documents as regards the approximative algorithms, each of which is incorporated herein by reference, in its entirety:

M. Kachelrieβ, S. Schaller, and W. A. Kalender, "*Advanced single-slice rebinning in cone-beam spiral CT*", Med. Phys. 27 (2000) 754-772

S. Schaller, K. Stierstorfer, H. Bruder, M. Kachelrieβ, and T. Flohr, "Novel approximate approach for high-quality image reconstruction in helical cone beam CT at arbitrary pitch", Proceedings SPIE 4322 (2001) 113-127

K. Stierstorfer, T. Flohr, H. Bruder, "*Segmented Multiple Plane Reconstruction—A Novel Approximate Reconstruction Scheme for Multi-slice Spiral CT*", Proceedings of Intern. Meeting on Fully 3-D Image Reconstruction in Radiology and Nuclear Medicine, Pacific Grove, Calif., USA, October, 30-Nov. 2, 2001, pp. 95-97.

An overview of the exact methods is set forth in the document by K. Sourbelle, H. Kudo, G. Lauritsch, K. C. Tam, M. Defrise, and F. Noo, "*Performance Evaluation of Exact Cone-Beam Algorithms for the Long-Object Problem in Spiral Computed Tomography*", Proceedings of Intern. Meeting on Fully 3-D Image Reconstruction in Radiology and Nuclear Medicine, Pacific Grove, Calif., USA, October, 30-Nov. 2, 2001, pp. 153-156, the entire contents of which are hereby incorporated herein by reference.

Approximative methods are distinguished by a high measure of practicability and flexibility. However, the inclination angle of the measuring rays to the axis of rotation (cone angle) is taken into account only approximately, for which reason the approximation error grows with the cone angle. It may be said overall that, starting from a certain number of detector rows, each approximative method will cause image artifacts, and thus leads to unsatisfactory image results. The exact methods take account without error of the cone-beam-like recording geometry both in the filter step and in the 3D back-projection. They achieve good image results that are independent of the cone angle occurring. However, it is disadvantageous that they are extremely complicated and very inflexible in application.

SUMMARY OF THE INVENTION

An object of an embodiment of the invention resides in finding an imaging method for a multi-slice spiral CT scan which on the one hand retains the good characteristics of the exact methods with reference to image quality, but on the other hand reduces the computational outlay through approximations and also increases the flexibility of the calculation as far as possible.

Exact methods can be formulated as an algorithm of filtered back projection (FBP) type. Examples of this are described in the documents, the entire contents of each of which are hereby incorporated herein by reference:

H. Kudo, F. Noo, and M. Defrise, "*Quasi-Exact Filtered Backprojection Algorithm for Long-Object Problem in Helical Cone-Beam Tomography*", IEEE Transactions on Medical Imaging 19 (2000) 902-921;

K. C. Tam "*Exact local regions-of-interest reconstruction in spiral cone-beam filtered-backprojection CT: theory*", Proceedings of the SPIE 3979 (2000), 506-519;

G. Lauritsch, K. C. Tam, K. Sourbelle, and S. Schaller, "*Exact local regions-of-interest reconstruction in spiral cone-beam filtered-backprojection CT: numerical implementation and first image results*", Proceedings of the SPIE 3979 (2000), 520-532.

In these exact methods, a detector image X is changed by a filter operation to a filtered detector image Y, and the filtered detector image Y is subsequently transmitted into a volumetric image via 3D back-projection.

Without restriction of generality, the following text describes the case of a planar detector that is defined by a coordinate system (u, v). The v-axis is parallel to the axis of rotation of a spiral track on which the radiation source and the detector move, and the u-axis is perpendicular to this axis of rotation. The filter step then includes $$Y = -D_{\vec{t}} \int_{\eta-\pi/2}^{\eta+\pi/2} d\theta B(\theta) P(\theta) M D_{\vec{R}(\theta)} X + Bt \qquad (1)$$

with $D_{\vec{e}}$ as the partial derivative in the direction of the vector $\vec{e}$, $\vec{t}$ as the projection of the spiral tangent onto the detector, $\eta$ as the angle of the vector $\vec{t}$ with the u-axis of the detector coordinate system, P(θ), B(θ) as the projection and back-projection on the detector along straight lines with $\vec{r}(\theta)$ as the normal vector, θ as the angle of the normal vector $\vec{r}(\theta)$ with the u-axis of the detector coordinate system, M as the masking operation, and V as a pair of masking lines such that detector pixels that do not lie between the masking lines V are set to zero in the masking operation, and Bt as the boundary term.

The masking lines V are yielded from the, cone-beam projection of the spiral track segments which are situated a full revolution before and after the current focal position. The masking line $V_{top}$ from the projection of the spiral segment above the current focal position is written in the form of the v-detector coordinate as a function of the u-detector coordinate as $$V_{top}(u) = \frac{\delta}{2\rho} \cdot h \cdot \left(1 + \frac{u^2}{\delta^2}\right) \cdot \left(\frac{1}{2} - \frac{1}{\pi}\arctan\frac{u}{\delta}\right) \qquad (2)$$

where δ is the distance from the focus to the detector,

ρ is the focal track radius, and h is the bed feed per spiral rotation.

The masking line $V_{bottom}$ from the projection of the spiral segment below the current focal position is yielded from the point reflection of $V_{top}$ at the detector coordinate origin $$V_{bottom}(u) = -V_{top}(-u) \qquad (3)$$

The boundary term Bt is given by $$Bt = D_{\vec{t}} \int_{\eta-\pi/2}^{\eta+\pi/2} d\theta B(\theta) \int_{-\infty}^{+\infty} ds(\theta)(D_{\vec{s}(\theta)}M)s(\theta)X \qquad (4)$$

where vector s(θ) is perpendicular to the normal vector $\vec{r}(\theta)$ of the projection straight line, and s(θ) is the coordinate value of the rotated detector coordinate system (r,s) (θ) defined by the vectors $\vec{r}(\theta)$ and $\vec{s}(\theta)$.

By using the product rule for derivatives $$D_{\vec{r}(\theta)}(MX) = M D_{\vec{r}(\theta)}(X) + D_{\vec{r}(\theta)}(M)X \qquad (5)$$

and the identity $$R_{\vec{t}} = -D_{\vec{t}} \int_{\eta-\pi/2}^{\eta+\pi/2} d\theta B(\theta)P(\theta)D_{\vec{r}(\theta)} \qquad (6)$$

where $R_{\vec{t}}$ is the ramp filter in the direction $\vec{t}$ on the projection of the spiral tangent, equation (1) is transformed into $$Y = R_{\vec{t}}M X + Bt + C \qquad (7)$$

where the correction term C is $$C = D_{\vec{t}} \int_{\eta-\pi/2}^{\eta+\pi/2} d\theta B(\theta)P(\theta)(D_{\vec{r}(\theta)}M)X. \qquad (8)$$

A consideration of the terms of equation (7) yields the following picture:

The term $R_{\vec{t}}MX$ can be calculated quickly and simply with the aid of known convolution methods. It is locally limited in the axial direction.

The boundary term Bt is easy to calculate. It is of infinite extent in the axial direction, and so the filtered detector image Y must be calculated in such an axial extent so that the cone beam projection of the volumetric image is completely contained therein. This leads to an increased complexity in the 3D back-projection. In addition, object points of the volumetric image are thereby artificially correlated, and this leads to the so-called "long object problem".

The correction term C is numerically sensitive and therefore complicated to calculate. Oversampling is required here, and this lengthens the computing time. The correction term is of infinite extent in the axial direction. The consequences have already been discussed above in conjunction with the boundary term Bt.

The inventors have now found that a substantial improvement in the practicability of the above-described exact method results when the boundary term Bt and the correction term C can be simplified. In particular, it is possible to avoid the infinite extent in the axial direction.

A fortunate insight of the inventors has shown that the term 2*(Bt+C) corresponds approximately to a term that alternately applies the masking M and filtering $R_{\vec{t}}$ to the detector image X, and subsequently forms the difference. It therefore holds that:

$$Bt + C \approx \frac{1}{2}(MR_{\vec{t}} - R_{\vec{t}}M)X. \qquad (9)$$

Substituting equation (9) in equation (7) yields the following simple filter rule:

$$Y = \frac{1}{2}(R_{\vec{t}}M + MR_{\vec{t}})X. \qquad (10)$$

The following advantages are achieved by applying this filter rule:

The two terms of equation (10) can be calculated easily and quickly by use of convolution methods.

The filtered detector image Y is locally limited in the axial direction. In addition to the savings in computing time in 3D back-projection, the "long object problem" is also thereby circumvented.

The approximation supplies good image quality up to relatively high cone angles, corresponding to a large number of detector rows.

The utilization of data redundancies in the case of reduced, discrete values of the bed feed is substantially easier than in the case of exact algorithms. As will be explained later, the approximation renders different weighting of some contributions unnecessary.

In order to carry out the method, it should be borne in mind that the application of the ramp filter $R_{\vec{t}}$ to a masked detector image MX requires a smoothing of the transition from the inner region of the mask with value 1 to the outer region with value 0, since the ramp filter generates image artifacts at discontinuous points. In order to avoid these image artifacts, the smoothed mask should have discontinuity neither in the mask itself nor in the first, partial derivative in the direction t of the ramp filter, at least. It is advantageously possible to use a $\sin^2$ function for a smooth transition, while it may be pointed out that other similar smoothing functions can also be used.

It is sometimes advantageous in medical applications to reduce the bed feed. In conjunction with the reduced bed feed, the aim is to increase the signal-to-noise ratio from measurement and allocation of redundant data. Neither the exact algorithm according to the equation (7) nor the approximation according to equation (10) offers the direct possibility of utilizing data redundancies, since the detector surface used in the case of reduced bed feed would shrink in accordance with the masking according to equations (2) and (3).

In the case of exact calculating methods, data redundancies can be used for specific discrete values of the bed feed. If the maximum bed feed $h_{max}$ is defined as the bed feed for which the surface marked out by the mask M is still covered by the detector, the existing data redundancies can be used in the case of discrete bed feed values $h_k$ of $$h_k = \frac{h_{max}}{2k+1}, \text{ with a natural number } k \geq 0. \quad (11)$$

The masked region is widened for this purpose. The mask $M_k$ is defined by the cone beam projection of the spiral track segments of the (k+1)th revolutions before and after the current focal position.

The masking line $V_{k,top}$ of the spiral track segment above the current focal position is given by $$V_{k,top}(u) = \frac{\delta}{2\rho} \cdot h_k \cdot \left(1 + \frac{u^2}{\delta^2}\right) \cdot \left(k + \frac{1}{2} - \frac{1}{\pi}\arctan\frac{u}{\delta}\right). \quad (12)$$

The symmetry relationship of equation (3) holds for the masking line $v_{k,bottom}$. Substituting equation (11) in equation (12) yields $$V_{k,top}(u) = \frac{\delta}{2\rho} \cdot h_{max} \cdot \left(1 + \frac{u^2}{\delta^2}\right) \cdot \left(\frac{1}{2} - \frac{1}{2k+1} \cdot \frac{1}{\pi}\arctan\frac{u}{\delta}\right). \quad (13)$$

The mask $M_k$ is always covered completely by that rectangular detector surface which also fully contains the mask $M=M_0$ of the maximum bed feed. A consideration of the volume that is covered by 3D back-projection of detector images masked in such a way reveals that the volumetric image is approximately covered (2k+1) times. The filter rule of equation (10) is changed in a simple way to $$Y = \frac{1}{2} \cdot \frac{1}{2k+1}(R_{\vec{t}} M_k + M_k R_{\vec{t}})X. \quad (14)$$

In accordance with the basic idea of an embodiment of the invention represented in detail above, the inventors propose to improve imaging methods, known per se, for a multi-slice spiral CT scan. An object to be examined is scanned with reference to its absorption behavior by a rotating ray bundle moving in the direction of the axis of rotation, and the measured absorption data are collected, in which case in order to reconstruct a volumetric image from the measured data, the latter are filtered and the filtered data are subsequently back-projected in three dimensions in order to produce a volumetric image of the object to be examined, the volumetric image representing absorption values, obtained from the data, of the voxels belonging to the volume of the object to be examined, for the radiation of the ray bundle. An improvement according to an embodiment of the invention now resides in the fact that the filtering is performed by multiple application of a ramp filter $R_{\vec{t}}$ and a masking operation M to a projection image in a different sequence.

In accordance with an advantageous design of the method, the ramp filter $R_{\vec{t}}$ and the masking operation M are applied alternately, in which case it is preferred to calculate the filtered detector image Y with the aid of the equation $$Y = \frac{1}{2}(R_{\vec{t}} M + M R_{\vec{t}})X$$

X representing the unfiltered detector image, $R_{\vec{t}}$ representing the ramp filtering in the direction of the projection of the spiral tangent, and M representing the masking.

In accordance with a further particular design of the method, the inventors propose that a bed feed $h_k$ for the relative movement of the focus and object to be examined in the direction of the axis of rotation of the focus is used whose value satisfies the condition $$h_k = \frac{h_{max}}{2k+1}$$

k being a natural number with $k \geq 0$, and $h_{max}$ corresponding to the bed feed for which a surface marked out by the mask still just covers the detector. By way of this condition, it is possible in the case of a linear bed feed with the discrete values $h_k$ for the filtering to be carried out with the aid of the rule:

$$Y = \frac{1}{2} \cdot \frac{1}{2k+1}(R_{\vec{t}} M_k + M_k R_{\vec{t}})X,$$

k representing the index number from the bed feed $h_k$, Y representing the filtered detector image, X representing the unfiltered detector image, $R_{\vec{t}}$ representing the ramp filter, and $M_k$ representing the masking, referred in each case to the index number k of the bed feed $h_k$.

Furthermore, it is proposed as a particularly advantageous design to undertake smoothing with reference to the masking. It is preferably possible here for the masking operation to be fashioned to correspond to a $\sin^2$ function in the transition region. In any case, a continuous function must be used for smoothing.

The smoothing can be performed in this case in one dimension in one direction, or twice consecutively in one dimension in two directions, the directions preferably being mutually perpendicular. Here, one-dimensional smoothings harbor the advantage of being less intensive computationally, and thus of being able to be carried out quickly. Alternatively, it is also possible to carry out two-dimensional smoothing, although this is admittedly more expensive in terms of computing power, but is somewhat more effectively fashioned for one run.

In addition to the method outlined above, the inventors propose a CT unit for scanning an object to be examined, which is equipped with a ray bundle emanating from at least one focus and with a detector array of planar design with a multiplicity of distributed detector elements for detecting the rays of the ray bundle, the at least one focus moving relative to the object to be examined on at least one focal track running around the object to be examined and with the detector array situated opposite. However, the CT unit is to have at least a device for collecting detector data, filtering and back-projection, the device for filtering being fashioned in such a way that the above-described method is carried out. The device for filtering are preferably at least partially implemented by programs or program modules.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
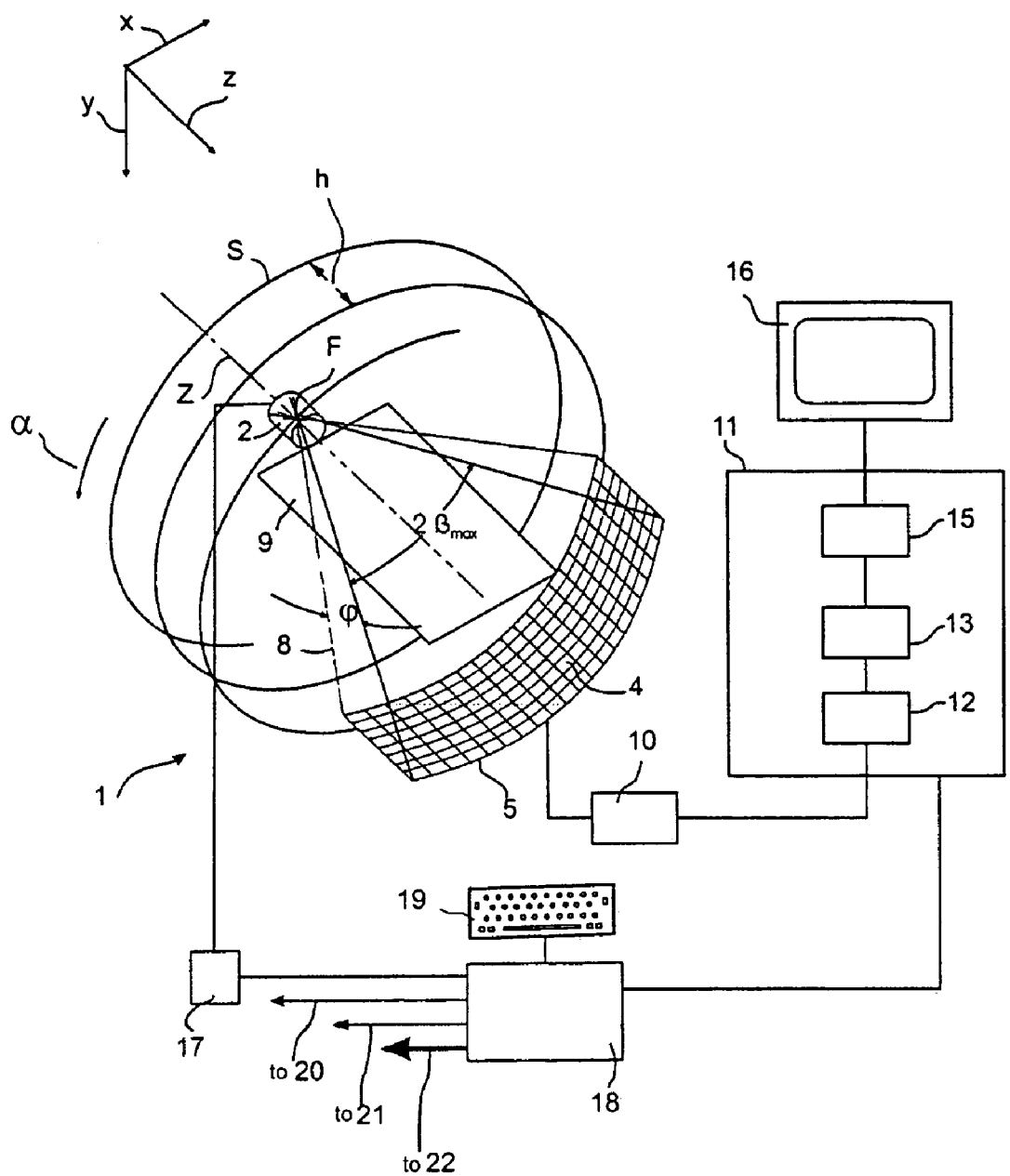
FIG. 1 shows multi-slice CT in a perspective illustration of the scanning unit and peripheral devices.
Figure 2:
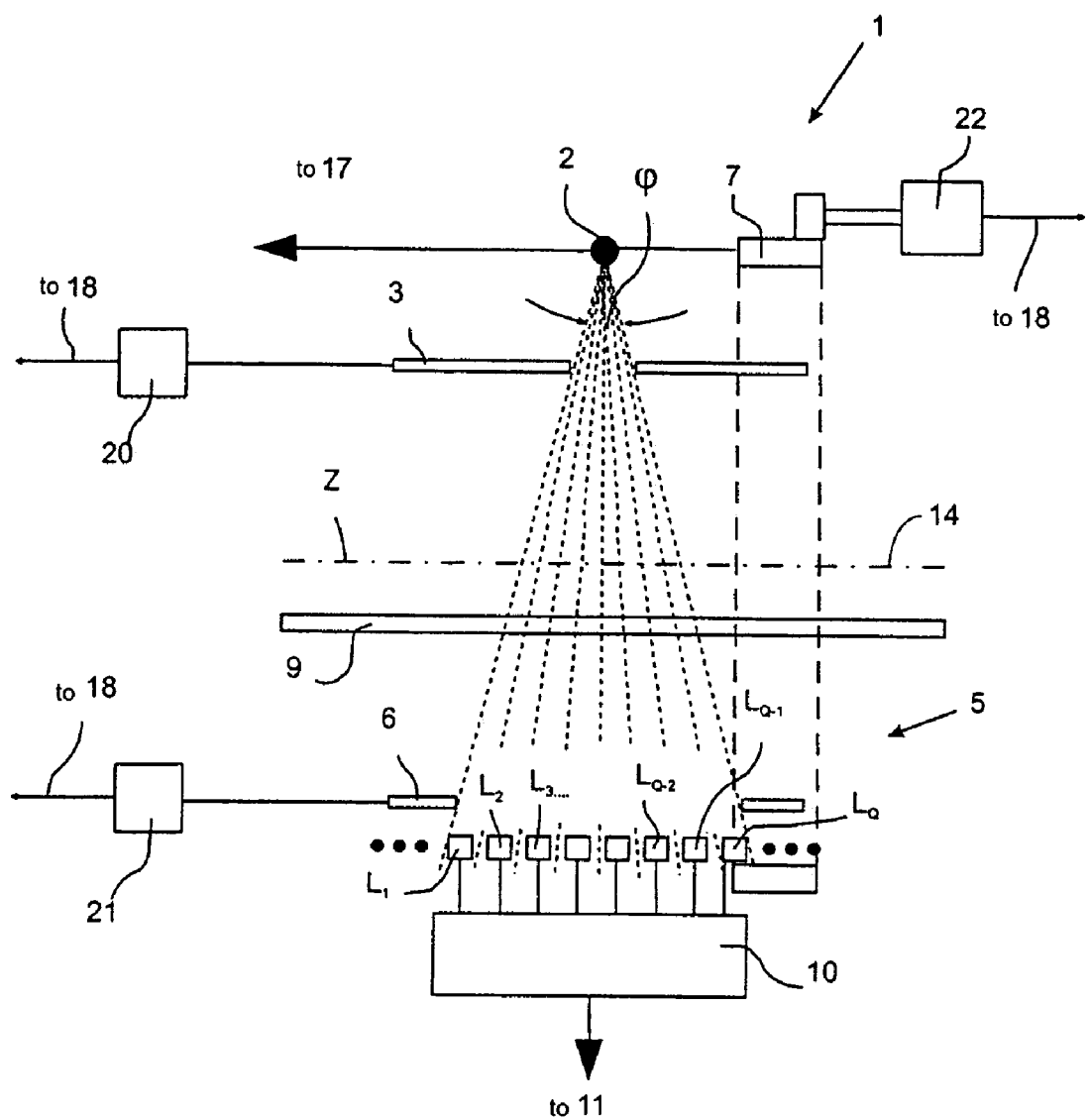
FIG. 2 shows a longitudinal section through the multi-slice CT from FIG. 1.

FIGS. 1 and 2 show a partially perspective illustration of a third—generation multi-slice CT unit for carrying out the method according to an embodiment of the invention. The measuring arrangement (=gantry) denoted by 1 has an X-ray source 2 with a beam diaphragm 3 positioned in front of and near it. This array of planar design having a plurality of rows and columns of detector elements forms the detector system 5 and is illustrated in section in FIG. 2 with a beam diaphragm 6 positioned in front of the detector system and near the detector. For the purpose of greater clarity, FIG. 1 illustrates only eight rows $L_1$ to $L_Q$ of detector elements 4. The detector system 5 can, however, also have another or preferably greater number of rows without departing from the scope of the invention. A different planar arrangement of the detectors is also likewise possible.

The X-ray source 2 with the beam diaphragm 3 on the one hand, and the detector system 5 with the beam diaphragm 6, on the other hand, are fitted on a rotary frame 7 opposite one another in such a way that a pyramid-shaped X-ray bundle whose edge rays are denoted by 8, which emanates from the X-ray source 2 during operation of the CT unit and is faded up by the adjustable beam diaphragm 3, strikes the detector system 5. In this case, the beam diaphragm 6 is set to correspond to the cross section of the X-ray bundle, set via the beam diaphragm 3, such that in accordance with different operating modes only that region of the detector system 5 is exposed which is struck directly by the X-ray bundle. Only eight rows of detector elements 4 are used in FIGS. 1 and 2, while the further rows, indicated by dots, are covered by the beam diaphragm 6 and therefore not active.

The X-ray bundle has a cone angle $\phi$, which is the aperture angle of the X-ray bundle in a plane containing the system axis Z and the focus F. The aperture angle of the X-ray bundle is $2\beta_{max}$ in a plane (fan aperture angle) situated at right angles to the system axis Z and containing the focus F.

The rotary frame 7 can be set in rotation about a system axis denoted by Z by way of a drive device 22. The system axis Z runs parallel to the z-axis of a coordinate system which is rectangular in three dimensions and illustrated in FIG. 1.

The columns of the detector system 5 likewise run in the direction of the z-axis, while the rows run transversely with respect to the system axis Z.

In order to be able to bring an object to be examined, for example a patient, into the beam path of the X-ray bundle, a support device 9 is provided which can be displaced parallel to the system axis Z, that is to say in the direction of the z-axis. Specifically, this is done in such a way as to obtain synchronization between the rotation movement of the rotary frame 7 and the translation movement of the support device such that the ratio of translation speed to rotation speed is adjustable by selecting a desired value of the feed h of the support device 9 per rotation of the rotary frame.

It is hence possible for a volume of an object to be examined, located on the support device 9, to be examined in accordance with a volume scan. It is possible to carry out the volume scan in the form of a spiral scan such that a multiplicity of projections from different projection directions are recorded by way of a measuring unit per revolution of the measuring unit 1, by simultaneous rotation of the measuring unit 1 and translation of the support device 9. During this spiral scan, the focus F of the X-ray source moves relative to the support device 9 on a spiral track S about the object to be examined.

During the spiral scanning, measured data which correspond to individual projections in cone-beam geometry are read out from the detector elements of each active row of the detector system 5, subjected to digital-to-analog conversion in a data processing unit 10, serialized and transmitted to an image computer 11.

After preprocessing of the measured data in a preprocessing unit 12 of the image computer 11, the resulting data stream passes to a volumetric image reconstruction unit 13 which uses the measured data to reconstruct images of the desired volume of the object to be examined by way of the computer operation to be described later.

The CT images are composed of voxels (voxel=volume element) assembled in a grid, by voxels being assigned to the respective image volume, each voxel being assigned a CT number in Hounsfield units (HU), and it being possible to represent the individual voxels according to the CT number/gray-value scale in a gray-scale value corresponding to its respective CT number. The image volume can be visualized in different ways.

In a simple form, arbitrary planes can be represented as tomographic images in any desired orientation. However, there are also more complex methods which visualize the entire volume.

Mention may be made here, by way of example, of the shaded surface display (SSD) and volume rendering (VR). SSD calculates in relation to a settable threshold value an isosurface for which the image volume has the threshold value. The isosurface can be represented on a display screen using methods of computer graphics.

In the case of VR, each voxel is assigned optical characteristics such as opacity and color that can be set in accordance with its value. Artificial views of the object defined in such a way are calculated using methods of computer graphics. A visualization unit 15 uses the volumetric data reconstructed by the image reconstruction unit 13 to calculate images and display them on a display unit 16, for example a monitor, connected to the image computer 11.

The X-ray source 2, for example an X-ray tube, is supplied by a generator unit 17 with the required voltages and currents, for example the tube voltage U. In order to be able to set these to the respectively required values, the generator unit 17 is assigned a control unit 18 with keyboard 19 that permits the required settings.

The other operation and control of the CT unit is also carried out by use of the control unit 18 and the keyboard 19, and this is illustrated by the fact that the control unit 18 is connected to the image computer 11.

Inter alia, it is possible to set the number of active rows of detector elements 4 and therefore the position of the beam diaphragms 3 and 6, for which the control unit 18 is connected to adjustment units 20 and 21 assigned to the beam diaphragms 3 and 6. It is also possible to set the rotation time τ which the rotary frame 7 requires for a full rotation, and this is illustrated by the fact that the drive unit 22 assigned to the rotary frame 7 is connected to the control unit 18.

Figure 3:
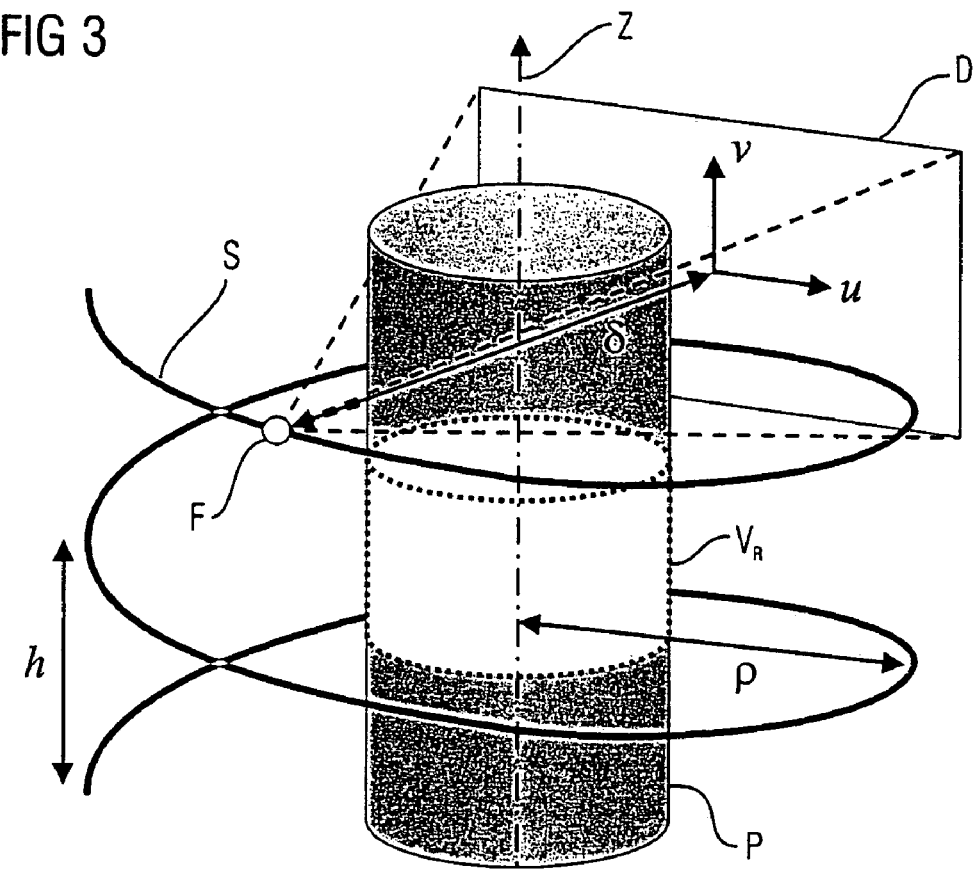
FIG. 3 shows an illustration of the recorded geometry of a spiral CT unit.
Figure 4:
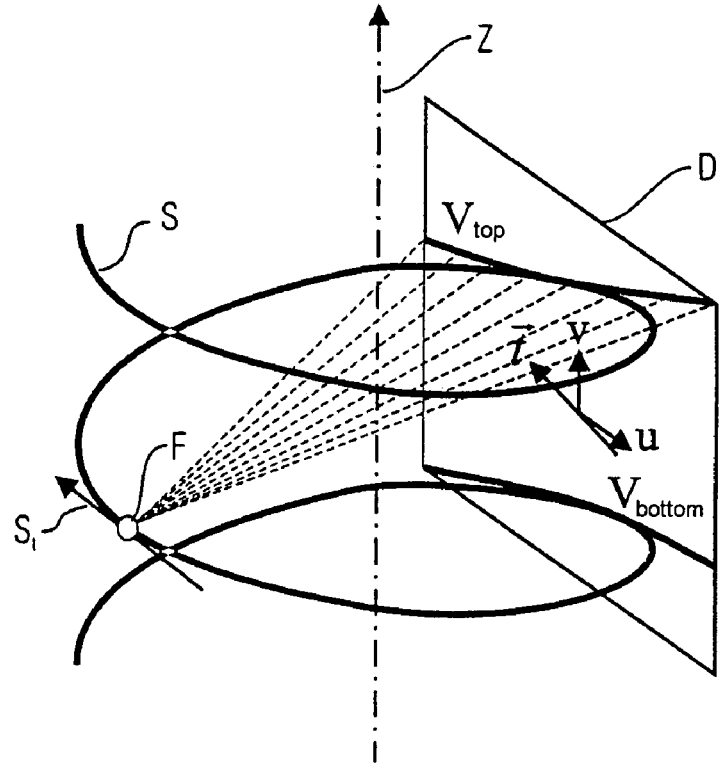
FIG. 4 shows an illustration of a masking operation.

The recording geometry of the spiral CT unit from FIGS. 1 and 2 is illustrated schematically in FIG. 3, the detector being reproduced only in a planar fashion here—as well as FIG. 4—for the sake of simplicity. The radiation source moves with its focus F along a spiral track S of pitch h, which corresponds to the bed feed, in a fashion rotating about an elongated object P to be examined, and in the direction of the system axis Z. In this process, the radiation intensity of the rays penetrating the object P to be examined is measured and collected on the detector D situated opposite. A volume $V_R$ to be reconstructed is embedded within the object P to be examined.

In order to reconstruct a volumetric image from the measured data, the latter must be filtered, and the filtered data must subsequently be back-projected in three dimensions in order to produce a volumetric image of the object to be examined, the volumetric image then representing absorption values, obtained from the data, of the voxels, belonging to the volume of the object to be examined, for radiation of the ray bundle.

According to an embodiment of the invention, the filtering can be performed by multiple application of a ramp filter $R_{\vec{t}}$ and a masking operation M to a projection image in a different sequence.

FIG. 4 illustrates such a masking operation via the detector data. The background is that during measurement only specific data of the measuring detector D are of interest for reconstruction, and additional information would have a disruptive effect. The data via the detector D are thus masked by a masking operation M in such a way that only the data lying inside the masking boundary lines $V_{top}$ and $V_{bottom}$ are retained. The upper and lower boundaries of the mask are formed in this case by the projection of the spiral track S onto the detector, starting from the focus F. In addition, the measured detector data are also further subjected to two-dimensional ramp filtering in the direction of the spiral tangent t projected onto the detector.

According to an embodiment of the invention, the detector data are then filtered before the reconstruction of the tomographic images, for example by the two-fold and inverse application of a ramp—filter and masking operation to the unfiltered detector data. Normalization in accordance with the number of operations is self-evident. A filter rule that is very easy, but comes very near to the exact computation solution, is thereby found.

Figure 5:
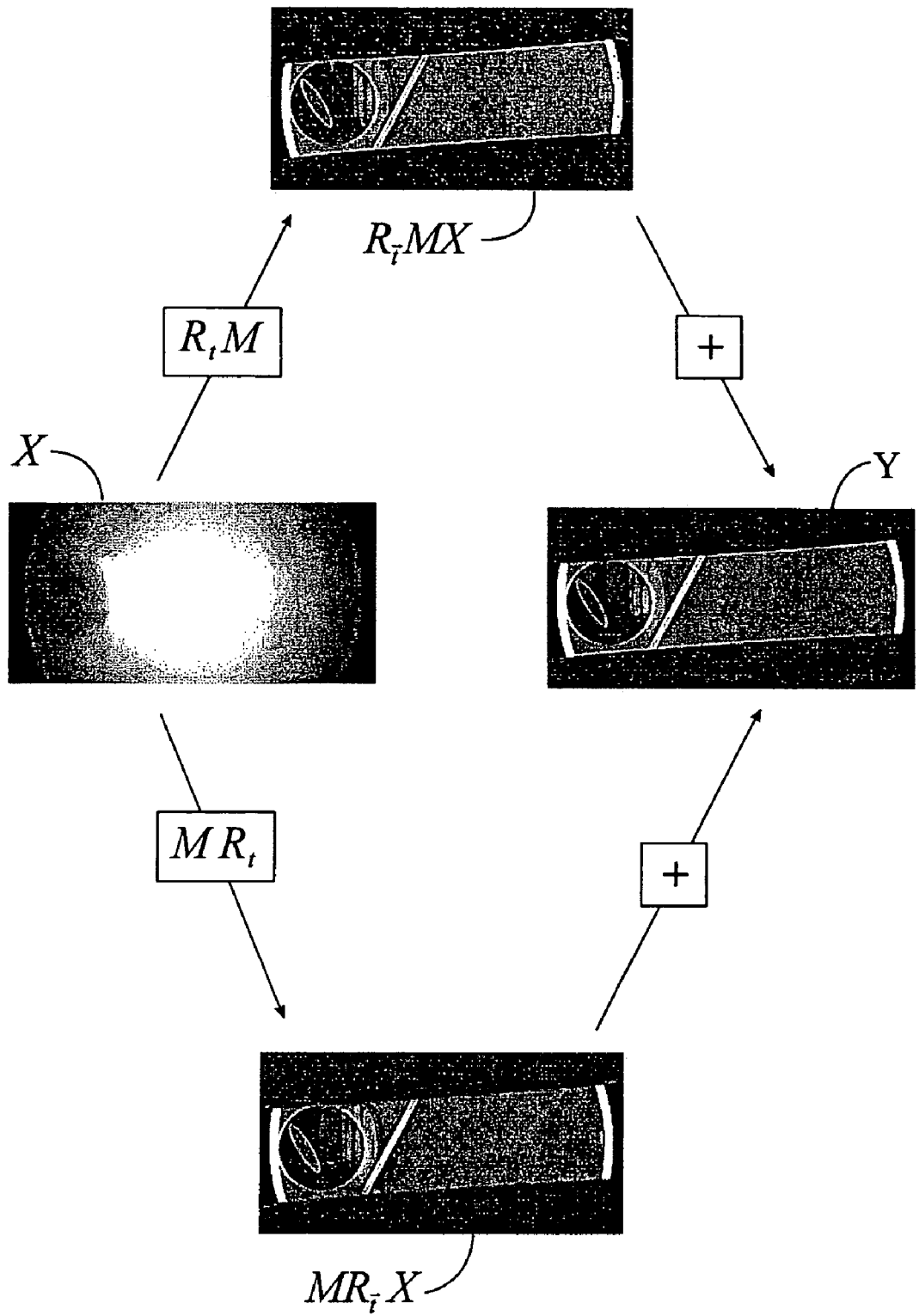
FIG. 5 shows an example of unfiltered and filtered detector data with the aid of a computer simulation.

FIG. 5 additionally illustrates the filter operation according to an embodiment of the invention for the sake of explanation. It shows first, on the left, an unfiltered detector image X, to which there was applied—with the arrow pointing upward—the masking operation N followed by the ramp filter $R_t$, the result being the detector image $R_tMX$. Also illustrated—with the arrow pointing downward—is the result of the same operations, carried out in reverse sequence, however, which yield the detector image $MR_tX$. The two results are subsequently added and normalized such that the finished, filtered detector image Y is yielded as end result by simple computing operations.

Thus, overall the known filtering of the detector data in the case of reconstruction methods, known per se, of volumetric images is replaced in the case of the method according to the invention by multiple application of a ramp filter $R_{\vec{t}}$ and a masking operation M to a projection image in a different sequence, and an imaging method is thereby disclosed for a multi-slice spiral CT scan which, on the one hand, retains the good characteristics of the exact methods with reference to the image quality, but on the other hand drastically reduces the outlay on calculation by the use of an approximation, thus also increasing the flexibility of the calculation.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging method for a multi-slice spiral CT scan, comprising:
    scanning an object to be examined with reference to the object's absorption behavior by a rotating ray bundle moving in a direction of an axis of rotation;
    collecting the measured absorption data;
    filtering the measured data to reconstruct a volumetric image from the measured data;
    back-projecting the filtered data in three dimensions; and
    generating a volumetric image of the object to be examined, the volumetric image representing absorption values obtained from data of voxels, belonging to a volume of the object to be examined, for radiation of the ray bundle, wherein
    the filtering is performed by multiple applications of a ramp filter $R_{\vec{t}}$ and a masking operation M to a projection image in different sequences.

2. The method as claimed in claim 1, wherein the ramp filter $R_{\vec{t}}$ and the masking operation M are applied alternately.

3. The method as claimed in claim 2, wherein the filtering is carried out using the rule:

$$Y = \frac{1}{2}(R_{\vec{t}}M + MR_{\vec{t}})X,$$

X representing the unfiltered detector image, $R_{\vec{t}}$ representing the ramp filtering in the direction of the projection of the spiral tangent, and M representing the masking.

4. The method as claimed in claim 2, wherein a bed feed $h_k$ is used whose value satisfies the condition:

$$h_k = \frac{h_{max}}{2k+1},$$

k being a natural number with $k \geq 0$, and $h_{max}$ corresponding to the bed feed for which a surface marked out by the mask just covers a detector.

5. The method as claimed in claim 4, wherein the filtering is carried out using the rule:

$$Y = \frac{1}{2} \cdot \frac{1}{2k+1}(R_{\vec{t}}M_k + M_k R_{\vec{t}})X,$$

where k is the index number from the bed feed $h_k$, Y is the filtered detector image, X is the unfiltered detector image, $R_{\vec{t}}$ is the ramp filter, and $M_k$ is the mask.

6. The method as claimed in claim 1, wherein the filtering is carried out using the rule:

$$Y = \frac{1}{2}(R_{\vec{t}}M + MR_{\vec{t}})X,$$

X representing the unfiltered detector image, $R_{\vec{t}}$ representing the ramp filtering in the direction of the projection of the spiral tangent, and M representing the masking.

7. The method as claimed in claim 1, wherein a bed feed $h_k$ is used whose value satisfies the condition:

$$h_k = \frac{h_{max}}{2k+1},$$

k being a natural number with $k \geq 0$, and $h_{max}$ corresponding to the bed feed for which a surface marked out by the mask just covers a detector.

8. The method as claimed in claim 7, wherein the filtering is carried out using the rule:

$$Y = \frac{1}{2} \cdot \frac{1}{2k+1}(R_{\vec{t}}M_k + M_k R_{\vec{t}})X,$$

where k is the index number from the bed feed $h_k$, Y is the filtered detector image, X is the unfiltered detector image, $R_{\vec{t}}$ is the ramp filter, and $M_k$ is the mask.

9. The method as claimed in claim 1, wherein the mask is smoothed at least in the mask's transition region by a continuous function.

10. The method as claimed in claim 9, wherein the smoothing of the originally discontinuous mask is performed in one dimension.

11. The method as claimed in claim 10, wherein the one-dimensional smoothing is performed multiply in different directions.

12. The method as claimed in claim 10, wherein the one-dimensional smoothing is performed multiply in mutually perpendicular directions.

13. The method as claimed in claim 9, wherein the smoothing of the originally discontinuous mask is performed in two dimensions.

14. A CT unit for scanning an object to be examined, comprising:
   a source emanating a ray bundle from at least one focus;
   a detector array of planar design with a multiplicity of distributed detector elements for detecting rays of the ray bundle, the at least one focus being adapted to move relative to the object to be examined on at least one focal track running around the object to be examined and with the detector array situated opposite thereto; and
   means for collecting detector data, filtering and 3D back-projecting the data, wherein the filtering is performed by multiple applications of a ramp filter $R_{\vec{t}}$ and a masking operation M to a projection image in a different sequences.

15. The CT unit as claimed in claim 14, wherein the means for filtering are implemented at least partially by at least one of a program and a program module.

16. An imaging device for a multi-slice spiral CT scan, comprising:
   means for scanning an object to be examined with reference to the object's absorption behavior by a rotating ray bundle moving in a direction of an axis of rotation;
   means for collecting measured absorption data;
   means for filtering the measured data to reconstruct a volumetric image from the measured data;
   means for back-projecting the filtered data in three dimensions; and means for generating a volumetric image of the object to be examined, the volumetric image representing absorption values obtained from data of voxels, belonging to a volume of the object to be examined, for radiation of the ray bundle, wherein
   the filtering is performed by multiple applications of a ramp filter $R_{\vec{t}}$ and a masking operation M to a projection image in different sequences.

* * * * *